United States Patent [19]

Satomi et al.

[11] 4,015,974
[45] Apr. 5, 1977

[54] AMIDO PHOSPHOROTHIOLATES

[75] Inventors: Takeo Satomi, Nishinomiya; Naganori Hino, Toyonaka; Koshi Tateishi, Minoo; Masachika Hirano, Toyonaka; Kunio Mukai, Nishinomiya; Katsuji Nodera, Takarazuka; Mitsuru Sasaki, Nishinomiya, all of Japan

[73] Assignee: Sumitomo Chemical Company, Limited, Osaka, Japan

[22] Filed: Sept. 30, 1975

[21] Appl. No.: 618,264

Related U.S. Application Data

[63] Continuation of Ser. No. 385,473, Aug. 3, 1973, abandoned.

[30] Foreign Application Priority Data

Aug. 5, 1972 Japan .................. 47-78666
May 24, 1973 Japan .................. 48-58833

[52] U.S. Cl. .................... 71/87; 260/293.85; 424/200
[51] Int. Cl.² .................. C07D 211/16
[58] Field of Search ........ 260/293.85; 424/200; 71/87

[56] References Cited

UNITED STATES PATENTS

| 3,134,801 | 5/1964 | Sehring et al. ............ 260/461 |
| 3,702,332 | 11/1972 | Pillon et al. ............ 260/347.7 |
| 3,763,284 | 10/1973 | Phillips ................. 260/934 |
| 3,776,984 | 12/1973 | Ratts .................... 260/943 |
| 3,784,563 | 1/1974 | Emerson et al. ............ 260/471 C |
| 3,806,560 | 4/1974 | Kishino et al. ............ 260/943 |
| 3,833,600 | 9/1974 | Toepfl ................... 260/293.85 |

FOREIGN PATENTS OR APPLICATIONS 941,636  11/1963  United Kingdom

Primary Examiner—G. Thomas Todd
Attorney, Agent, or Firm—Wenderoth, Lind & Ponack

[57] ABSTRACT

The present invention relates to compounds of the formula:

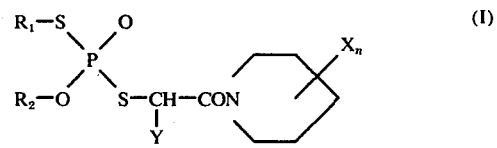

wherein $R_1$ is lower alkyl, lower alkenyl, lower alkynyl, cycloalkyl, unsubstituted aralkyl, lower alkyl or halogen-substituted aralkyl or halogen-substituted alkenyl; $R_2$ is lower alkyl; Y is hydrogen or methyl and X is lower alkyl; n is an integer of 1 to 5, and a method of producing these compounds. These compounds are eminently suited for killing weeds, injurious insects, nematodes and acaricides.

13 Claims, No Drawings

AMIDO PHOSPHOROTHIOLATES

This is a continuation of application Ser. No. 385,473, filed August 3, 1973, now abandoned.

The present invention relates to new compounds, herbicides, insecticides, acaricides and nematocides characterized by containing a new phosphorothiolate derivative as an active ingredient and the preparation thereof.

More particularly, the present invention provides
1. a new phosphorothiolate derivative of the formula

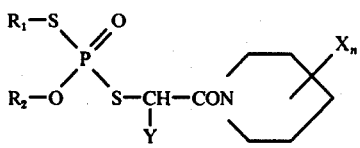

wherein $R_1$ is lower alkyl, lower alkenyl, lower alkynyl, cycloalkyl, unsubstituted aralkyl, lower alkyl or halogen-substituted aralkyl or halogen-substituted alkenyl; $R_2$ is lower alkyl; Y is hydrogen or methyl; X is lower alkyl; n is an integer of 1 to 5, 2. the preparation of the compound of the formula (I) characterized in condensing a salt of thiophosphate of the formula;

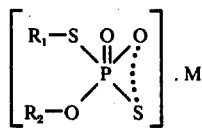

wherein $R_1$ and $R_2$ are the same as defined above, and M is an alkali metal with a halogenated acetoamide compound of the formula;

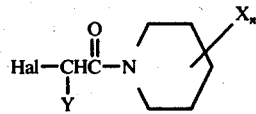

wherein Y, X and n are the same as defined above, and Hal is a halogen atom, and 3. a herbicidal, insecticidal, acaricidal and nematocidal composition containing the compound of the formula (I) as an active ingredient.

A preferred range of the compound of the formula (I) is as follows:

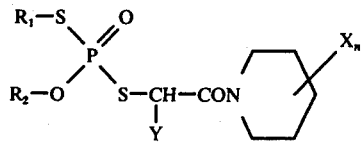

wherein $R_1$ is $C_1 - C_8$ straight or branched chain alkyl, allyl, chloroallyl, methallyl, propargyl, cyclohexyl, benzyl, α-methylbenzyl, phenethyl, β-methylphenethyl, chlorobenzyl, dichlorobenzyl, bromobenzyl or $C_1 - C_4$ alkyl substituted benzyl; $R_2$ is $C_1 - C_4$ alkyl; Y is hydrogen or methyl; X is methyl or ethyl; n is an integer of 1 to 3.

And a preferred compound as a herbicide is as follows:

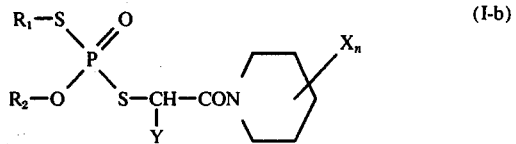

wherein $R_2$ is an alkyl group; $R_1$ is lower alkyl, cycloalkyl, lower alkenyl, halogen-substituted alkenyl, lower alkynyl or phenyl lower alkyl group; Y is a hydrogen atom or methyl group; X is a lower alkyl group; and n is in integer of 1 to 3.

Especially a compound of the formula;

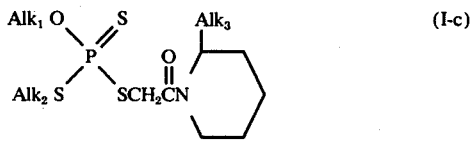

wherein $Alk_1$ is a $C_1 - C_4$ alkyl; $Alk_2$ is a $C_1 - C_5$ alkyl; $Alk_3$ is a $C_1 - C_2$ alkyl; has the most excellent herbicidal activity of the compound represented by the formula (I - b) without phytotoxity and toxity to warm-blood animals.

The new active ingredient of the present invention displays a strong herbicidal activity not only when used in both a pre-emergence treatment and a foliage treatment of weeds, but also on various kinds of weed including grassy weeds such as barnyard glass (*Echinochloa crusgalli*), large crabgrass (*Digitaria sanguinalis*), goose grass (*Eleusine indica*), water foxtail (*Alopecurus aequalis*) and annual bluegrass (*Poa annua*); broadleaved weeds such as redroot pigweed (*Amaranthus retroflexus*), common purslane (*Portulaca oleracea*), smart weed sp. (*Poligonum sp.*), common lambsquarter (*Chenopodium album*), and weeds in paddy field such as false pimpernel (*Linderna pyxidaria*), monochoria (*Monochoria viaginalis presl.*) and toothcut (*Rotala indica Koehue*); sedge weeds such as nutsedge sp. (*Cyperus difforuds*) and slender spikerush (*Eleocharis acicularis*).

One of the most important properties of herbicides is that they can display a herbicidal activity on various kinds of weed, because, if they can control most kinds of weed but not a few other kinds of weed, the remaining weeds will often grow and do harm to crops.

Therefore, the compounds of the present invention, which can display a strong herbicidal activity on more kinds of weed, can be said most suitable for a herbicide.

As for the insecticidal effect of the present compounds, they have a strong controlling effect on insects injurious to agriculture such as aphids, stan-borers and armyworms and cutworms; insects injurious to sanitation such as cockroaches, and houseflies; insects injurious to stored cereals; mites; and nematodes. Consequently they are effectively used as a herbicide, insecticide, acaricide and nematocide.

The present invention (1) relates to a herbicide, insecticide, acaricide and nematocide completed based on the above-mentioned information which contain the compounds represented by the formula (I) as an active ingredient.

There were known as relating prior arts to the present invention Belg. Patent No. 767,132 and Swiss Patent No. 496,398. The Belg. patent sayd phosphorodithiolate compounds having unsubstituted piperizino moisty have insecticidal, acaricidal and nematocidal activity, but present inventors have found that alkyl-substituted on that piperidin ring compounds, azepine compounds and tetrahydro quinoline compounds have unexpected excellent herbicidal activity. And it is unobvious from the prior art.

The Swiss Patent No. 496,398 says Thionothiolate type compounds have herbicidal activity, but Dithiolate type compound and Thiolate type compound of the present invention have the different structure.

The present invention (1) and (3) relate to a herbicidal, insecticidal, acaricidal and nematocidal composition completed based on the above-mentioned information which contain the compound represented by the formula (I) as an active ingredient.

The present invention (2) relates to a method for producing a compound of the formula (I) with a herbicidal insecticidal, acaricidal and nematocidal activity characterized in that phosphorodithiolate of the formula:

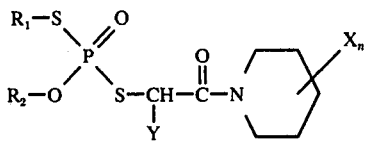

wherein $R_1$, $R_2$, Y, X and n are the same as defined above, is obtained by condensing a salt of dithiophosphate of the formula (II);

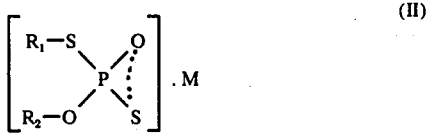

wherein $R_1$, $R_2$ and M are the same as defined above, with a halogenated acetoamide compound of the formula (III);

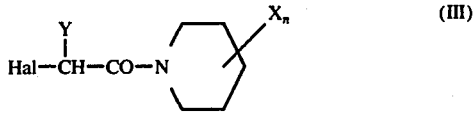

wherein Hal, Y, X and n are the same as defined above.

The present invention (2) can preferably be carried out by condensing a salt of dithiophosphate of the formula (II) with halogenated acetamide compound of the formula (III) in the presence of solvents such as water, alcohols, ketones and if possible solvents which can dissolve the both starting materials completely therein. The reaction temperatures and reaction times vary depending upon the kinds of solvent and starting material, and in general the reaction can satisfactorily proceed at 20° to 100° C. for one to several hours. On completion of the reaction, the aimed products can readily be obtained in a very high purity by conventional treatments, however, if necessary, can further be purified by column-chromatography.

Some examples of the starting materials, i.e. dithiophosphate salts and halogenated acetamides, which are used in the practice of the present invention will be shown as follows.

First, examples of dithiophosphate salt are as follows, which are only illustrative but not limitative thereto:
potassium O-ethyl-S-n-propylphosphorodithioate
potassium O-ethyl-S-iso-propylphosphorodithioate
potassium O-ethyl-S-butylphosphorodithioate
potassium O-ethyl-S-sec-butylphosphorodithioate
potassium O-ethyl-S-iso-butylphosphorodithioate
potassium O-ethyl-S-ethylphosphorodithioate
potassium O-ethyl-S-methylphosphorodithioate
potassium O-ethyl-S-iso-amylphosphorodithioate
potassium O-ethyl-S-n-octylphosphorodithioate
potassium O-ethyl-S-cyclohexylphosphorodithioate
potassium O-ethyl-S-cyclopentylphosphorodithioate
potassium O-ethyl-S-allylphosphorodithioate
potassium O-ethyl-S-propargylphosphorodithioate
potassium O-ethyl-S-methallylphosphorodithioate
potassium O-ethyl-S-2-chloropropenylphosphorodithioate
potassium O-ethyl-S-benzylphosphorodithioate
potassium O-ethyl-S-β-phenylethylphosphorodithioate
potassium O-n-propyl-S-n-propylphosphorodithioate
potassium O-n-propyl-S-n-butylphosphorodithioate
potassium O-n-propyl-S-allylphosphorodithioate
potassium O-n-propyl-S-β-phenylethylphosphorodithioate
potassium O-n-propyl-S-iso-propylphosphorodithioate
potassium O-n-propyl-S-sec-butylphosphorodithioate
sodium O-n-butyl-S-ethylphosphorodithioate
sodium O-n-butyl-S-n-propylphosphorodithioate
sodium O-n-butyl-S-iso-propylphosphorodithioate
sodium O-n-amyl-S-n-propylphosphorodithioate
sodium O-methyl-S-n-propylphosphorodithioate
sodium O-methyl-S-n-butylphosphorodithioate
sodium O-methyl-S-iso-propylphosphorodithioate
sodium O-ethyl-S-n-propylphosphorodithioate
sodium O-ethyl-S-n-butylphosphorodithioate
sodium O-ethyl-S-iso-propylphosphorodithioate
sodium O-ethyl-S-sec-butylphosphorodithioate
sodium O-n-propyl-S-n-propylphosphorodithioate
sodium O-n-propyl-S-n-butylphosphorodithioate
potassium o-ethyl-S-(4-chlorobenzyl)-phosphorodithioate
potassium O-ethyl-S-(4-tert-butylbenzyl)-phosphorodithioate
potassium O-ethyl-S-(4-methylbenzyl)-phosphorodithioate
potassium O-ethyl-S-(4-ethylbenzyl)-phosphorodithioate
potassium O-ethyl-S-(2-chlorobenzyl)-phosphorodithioate
potassium O-methyl-S-(4-chlorobenzyl)-phosphorodithioate
potassium O-methyl-S-(4-tert-butylbenzyl)-phosphorodithioate
potassium O-n-propyl-S-(4-chlorobenzyl)-phosphorodithioate
potassium O-n-propyl-S-(4-methylbenzyl)-phosphorodithioate
potassium O-n-butyl-S-(4-methylbenzyl)-phosphorodithioate sodium O-ethyl-S-(3,4-dichlorobenzyl)-phosphorodithioate sodium O-ethyl-S-(4-methylbenzyl)-phosphorodithioate Examples of halogenated acetamide compound are as follows, which are only illustrative but not limitative thereto:

2-methylpiperidine-α-chloroacetamide
3-methylpiperidine-α-chloroacetamide
4-methylpiperidine-α-chloroacetamide
2-ethylpiperidine-α-chloroacetamide
2-n-propylpiperidine-α-chloroacetamide
2,6-dimethylpiperidine-α-chloroactamide
2,4,6-trimethylpiperidine-α-chloroacetamide
2-methylpiperidine-α-bromoacetamide
3-methylpiperidine-α-bromoacetamide
4-methylpiperidine-α-bromoacetamide
2-methylpiperidine-α-iodoacetamide Next, some representative examples of the organo phosphoric acid ester of the present invention will concretely be shown as follows.

1 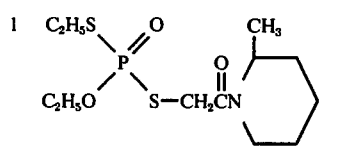

2 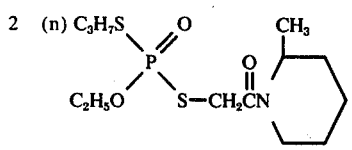

3 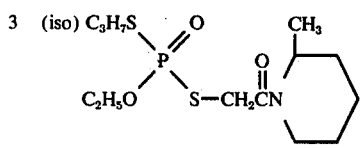

4 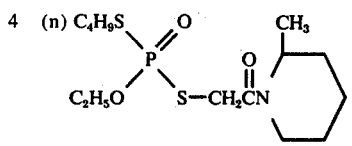

5 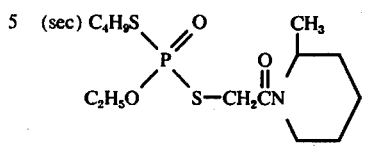

6 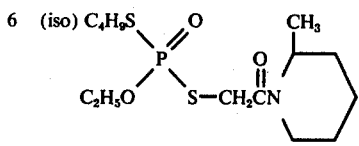

7 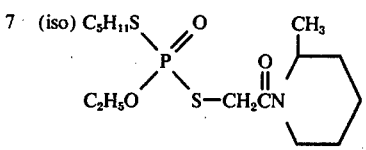

8 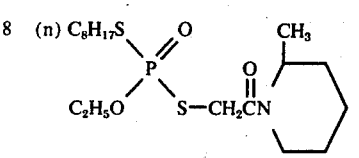

9 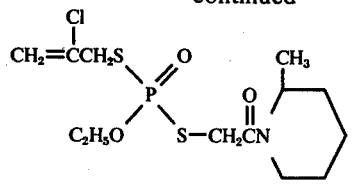

10 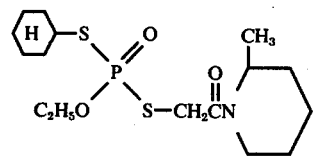

11 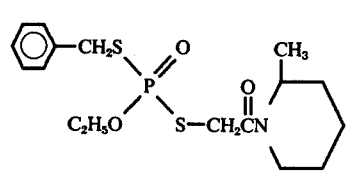

12 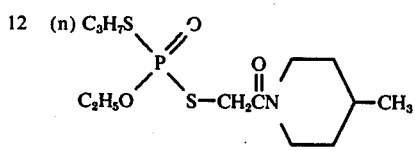

13 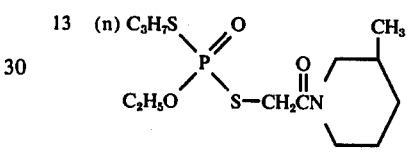

14 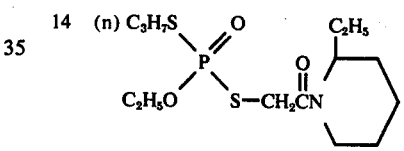

15 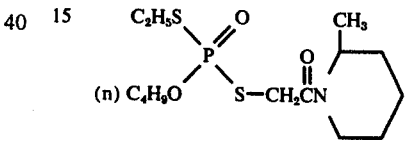

16 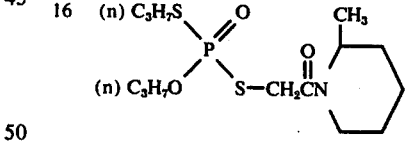

17 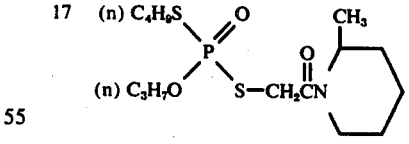

18 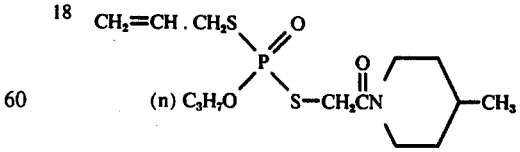

19 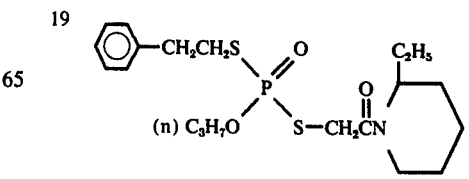

-continued
20 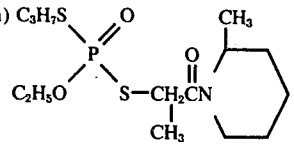
21 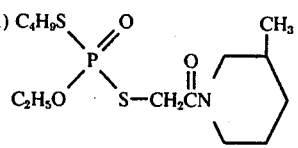
22 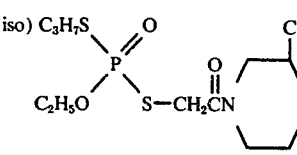
23 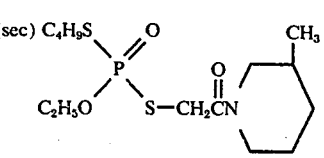
24 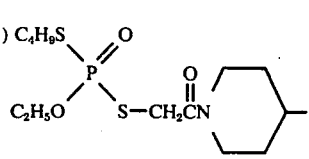
25 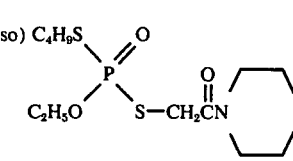
26 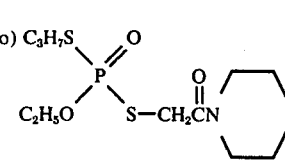
27 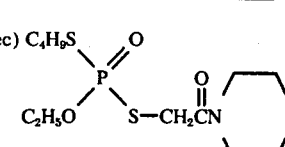
28 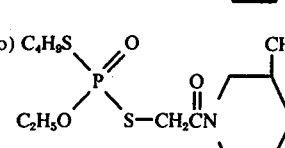
29 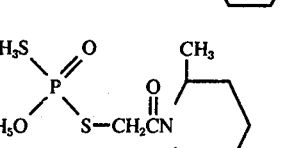
30 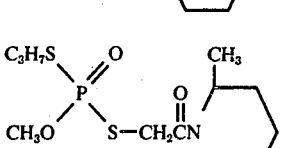
-continued
31 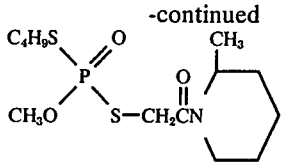
32 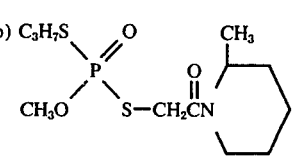
33 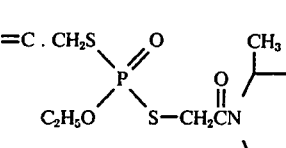
34 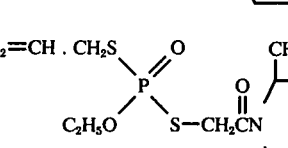
35 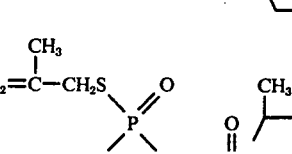
36 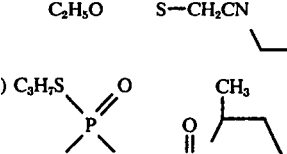
37 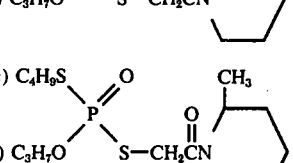
38 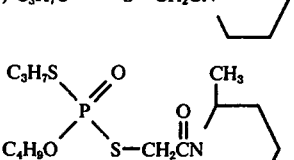
39 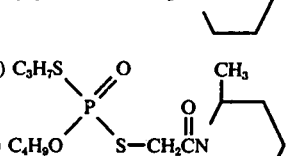
40 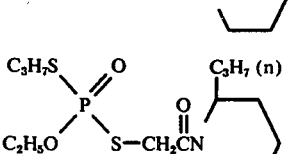
41 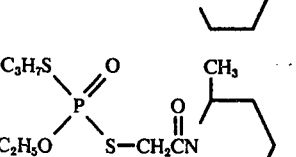

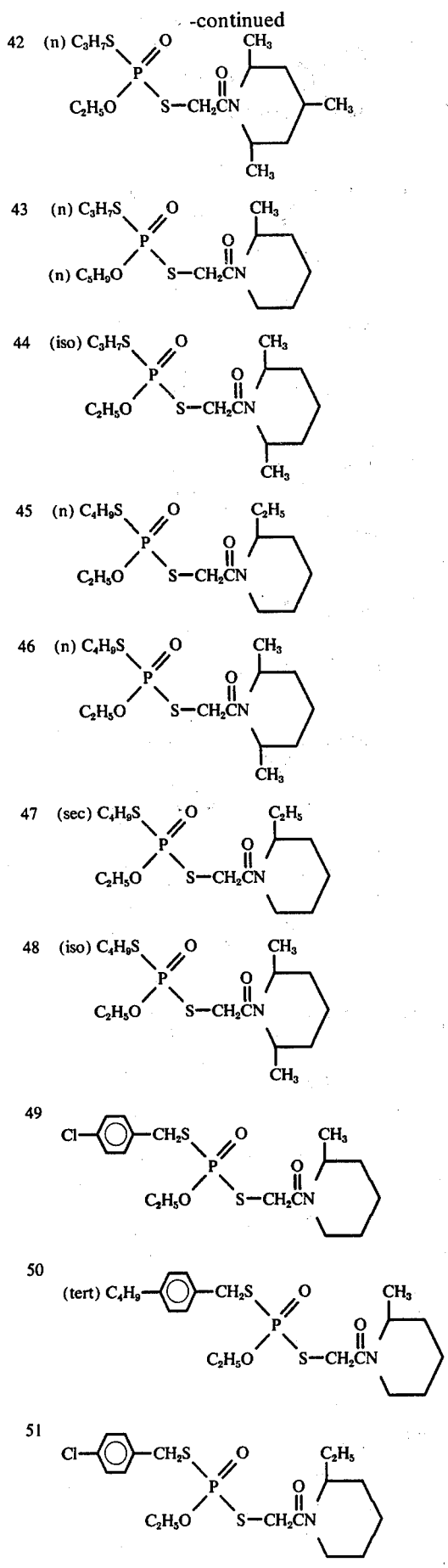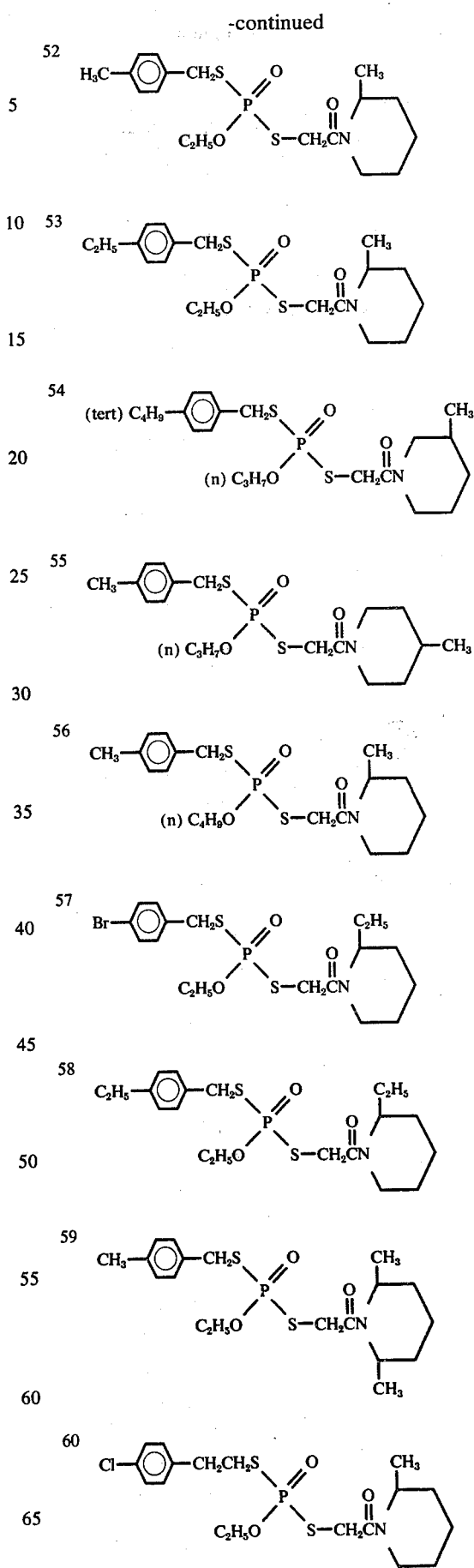

-continued
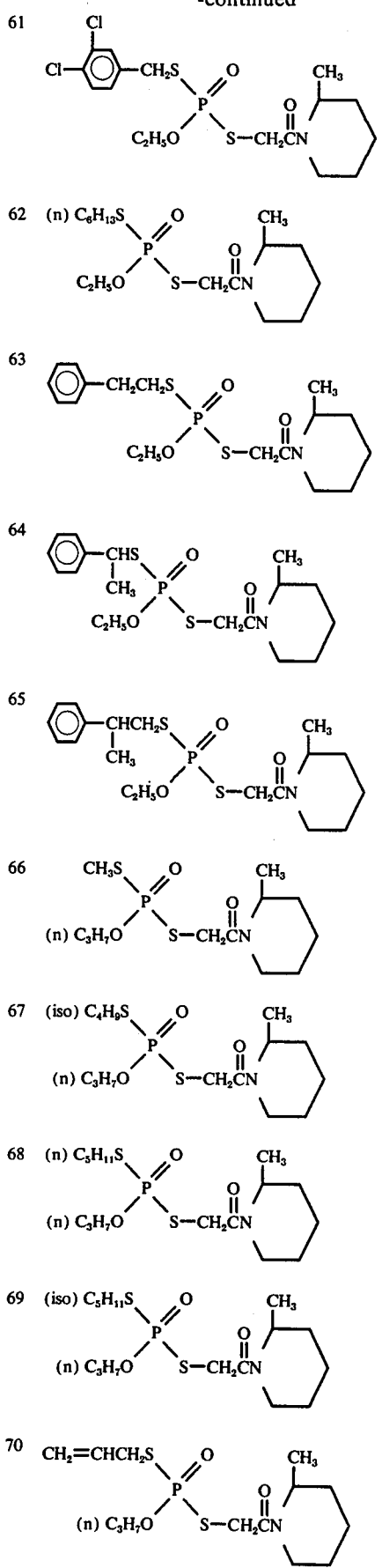
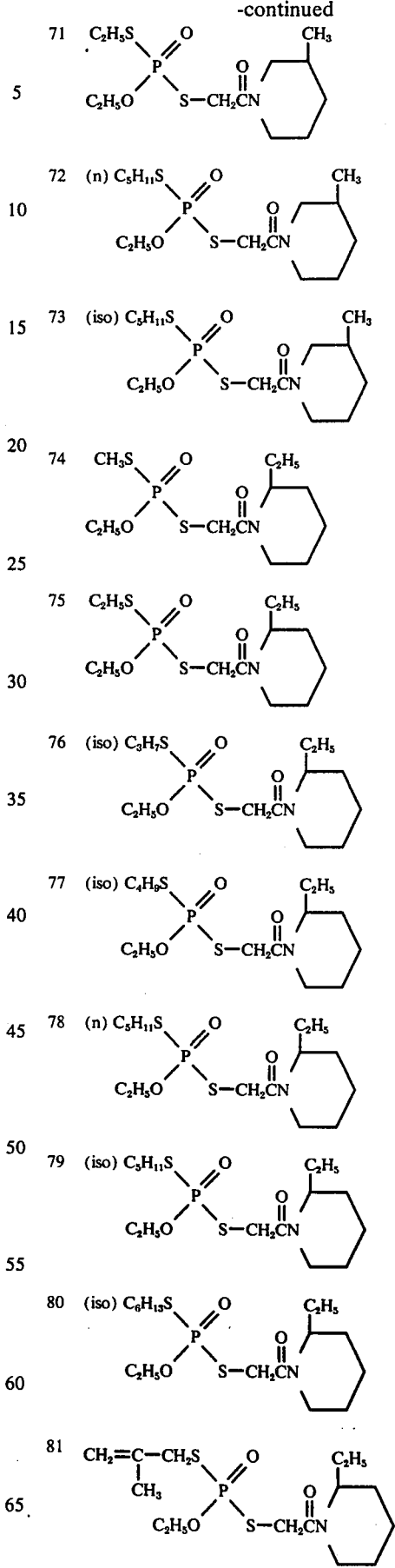

The compounds of the present invention, as described above, display a strong herbicidal activity on various kinds of weed, however one of the most noticeable features thereof is their herbicidal activity on more kinds of weed in addition to their strong herbicidal activity.

Moreover, the compounds of the present invention have other excellent properties as a herbicide, for example, a long persistency, an activity on both a pre-emergence treatment and a foliage treatment of weeds, and a selectivity to many crops such as rice plant, radish, soy bean, pea, tomato, wheat and corn. The present compounds are also useful as a herbicide for, needless to say, paddy rice fields, and cereals, vegetables, orchards, turfs, pasture lands, woods and forests and non-crop lands.

The features of the present compounds as an insecticide, acaricide and nematocide are that they have a controlling effect on various kinds of insect, a wide insecticidal spectrum, a particularly strong lethal effect on insects of Lepidoptera such as stem-borers and armyworms and cutworms, a strong lethal effect in both a spraying or dusting and a soil treatment, and a long persistency.

The present compounds, in actual application thereof, may be used as they are or may be used in any preparation form of dusts, granules, fine granules, wettable powders and emulsifiable concentrates. In formulating those preparations, there are used solid carriers including talc, bentonite, clay, kaolin, diatomaceous earth, vermiculite and calcium hydroxide; and liquid carriers including benzene, alcohols, acetone, xylene, methylnaphthalene, dioxane and cyclohexanone.

In actual application, the present compounds may be enhanced and ensured in effectiveness by using them in condition with surfactants such as spreaders for agriculture. It is also possible to use the present compounds in combination with agricultural chemicals such as fungicides, microbial insecticides, prechroide type insecticides, other insecticides and other herbicides, or with fertilizers.

The compositions of the present invention will be illustrated with reference to the following preparation examples.

Preparation 1

25 parts of the compound (2), 5 parts of a surfactant of polyoxyethylene acetylallylester type and 70 parts of talc were thoroughly mixed together by pulverizing to obtain a wettable powder.

Preparation 2

30 parts of the compound (3), 20 parts of a surfactant of polyethylene glycolester type and 50 parts of cyclohexanone were thoroughly mixed together to obtain an emulsifiable concentrate.

Preparation 3

5 parts of the compound (5), 40 parts of bentonite, 50 parts of clay and 5 parts of sodium lignosulfonate were thoroughly mixed together by pulverizing, sufficiently kneaded with water, granulated and dried to obtain granules.

Preparation 4

3 parts of the compound (12) and 97 parts of clay were thoroughly mixed together by pulverizing to obtain dusts.

Preparation 5

5 parts of the compound (15), 4 parts of sodium lignosulfonate, 86 parts of clay and 5 parts of water were thoroughly kneaded in a ribbon mixer and dried to obtain fine granules.

Preparation 6

25 parts of the compound (50), 5 parts of a surfactant of polyoxyethylene acetylallylester type and 70 parts of talc were thoroughly mixed together by pulverizing to obtain a wettable powder.

The present invention will be illustrated in more details with reference to the following test examples, in which the names of compound are represented by the numbers of the compound exemplified above.

Test Example 1: Pre-Emergence application.

Seeds of barnyard grass (*Echinochloa crus-galli*) and large crabgrass (*Digitaria sanguinalis*) as representatives of grassy weeds and those of radish, redroot pigweed (*Amaranthus retroflexus*), common purslane (*Portulaca oleracea*) and common lambsquarter (*Chenopodium album*) as representatives of broad-leaved weeds were individually sowed in flower pots of about 10 cm. in diameter. After covering the seeds with soil, test compounds as shown in Table 1 were individually applied to the soil treatment. Thereafter the plants were grown in a green house and 20 days after application the herbicidal effects of the compounds were observed, the results of which are as shown in Table 1.

Herbicidal effects were evaluated by the numerals ranging from 0 (not damaged) to 5 (completely killed). All the test compounds were used in the form of wettable powder and diluted with water before application.

Table 1

| Comp. No. | Amount applied (g./a.) | Barnyard grass | Large crab-grass | Radish | Redroot pigweed | Common purslane | Common lambs-quarter |
|---|---|---|---|---|---|---|---|
| | 40 | 5 | 5 | 0 | 5 | 5 | 5 |
| 1 | 20 | 5 | 5 | 0 | 5 | 4 | 4 |
| | 10 | 5 | 5 | 0 | 4 | 4 | 4 |
| | 40 | 5 | 5 | 1 | 5 | 5 | 5 |
| 2 | 20 | 5 | 5 | 0 | 5 | 5 | 5 |
| | 10 | 5 | 5 | 0 | 5 | 5 | 5 |
| | 40 | 5 | 5 | 0 | 5 | 5 | 5 |
| 3 | 20 | 5 | 5 | 0 | 5 | 5 | 5 |
| | 10 | 5 | 5 | 0 | 4 | 5 | 5 |
| | 40 | 5 | 5 | 0 | 4 | 5 | 5 |
| 4 | 20 | 5 | 5 | 0 | 4 | 4 | 4 |
| | 10 | 4 | 5 | 0 | 4 | 4 | 4 |
| | 40 | 5 | 5 | 0 | 5 | 5 | 5 |
| 5 | 20 | 5 | 5 | 0 | 5 | 5 | 5 |
| | 10 | 5 | 5 | 0 | 5 | 5 | 5 |
| | 40 | 5 | 5 | 0 | 5 | 5 | 5 |
| 7 | 20 | 5 | 5 | 0 | 5 | 5 | 5 |
| | 10 | 5 | 5 | 0 | 4 | 5 | 5 |
| | 40 | 5 | 5 | 0 | 4 | 4 | 4 |
| 8 | 20 | 4 | 4 | 0 | 4 | 4 | 4 |
| | 10 | 4 | 4 | 0 | 3 | 4 | 3 |
| | 40 | 5 | 5 | 0 | 5 | 5 | 5 |
| 9 | 20 | 5 | 5 | 0 | 5 | 5 | 5 |
| | 10 | 5 | 5 | 0 | 4 | 5 | 4 |
| | 40 | 5 | 5 | 0 | 4 | 4 | 4 |
| 10 | 20 | 4 | 4 | 0 | 4 | 4 | 4 |
| | 10 | 4 | 4 | 0 | 3 | 3 | 3 |
| | 40 | 5 | 5 | 0 | 5 | 5 | 5 |
| 11 | 20 | 5 | 5 | 0 | 5 | 4 | 4 |
| | 10 | 4 | 4 | 0 | 4 | 4 | 4 |
| | 40 | 5 | 5 | 0 | 5 | 5 | 5 |

Table 1-continued

| Comp. No. | Amount applied (g./a.) | Barnyard grass | Large crab-grass | Radish | Redroot pigweed | Common purslane | Common lambs-quarter |
|---|---|---|---|---|---|---|---|
| 12 | 20 | 5 | 5 | 0 | 5 | 5 | 5 |
|  | 10 | 5 | 5 | 0 | 4 | 5 | 5 |
| 13 | 40 | 5 | 5 | 0 | 5 | 5 | 5 |
|  | 20 | 5 | 5 | 0 | 5 | 5 | 5 |
|  | 10 | 5 | 5 | 0 | 4 | 4 | 4 |
| 14 | 40 | 5 | 5 | 0 | 5 | 5 | 5 |
|  | 20 | 5 | 5 | 0 | 5 | 5 | 5 |
|  | 10 | 5 | 5 | 0 | 4 | 5 | 4 |
| 15 | 40 | 5 | 5 | 0 | 5 | 5 | 5 |
|  | 20 | 5 | 5 | 0 | 5 | 5 | 5 |
|  | 10 | 5 | 5 | 0 | 4 | 5 | 4 |
| 16 | 40 | 5 | 5 | 0 | 4 | 4 | 5 |
|  | 20 | 4 | 5 | 0 | 4 | 4 | 4 |
|  | 10 | 4 | 5 | 0 | 4 | 4 | 4 |
| 17 | 40 | 5 | 5 | 0 | 4 | 4 | 5 |
|  | 20 | 4 | 5 | 0 | 4 | 4 | 4 |
|  | 10 | 4 | 4 | 0 | 3 | 3 | 4 |
| 18 | 40 | 5 | 5 | 0 | 5 | 5 | 5 |
|  | 20 | 5 | 5 | 0 | 4 | 4 | 5 |
|  | 10 | 4 | 5 | 0 | 4 | 4 | 4 |
| 19 | 40 | 5 | 5 | 0 | 4 | 4 | 4 |
|  | 20 | 4 | 4 | 0 | 4 | 4 | 4 |
|  | 10 | 4 | 4 | 0 | 4 | 4 | 3 |
| 22 | 40 | 5 | 5 | 0 | 5 | 4 | 5 |
|  | 20 | 5 | 5 | 0 | 4 | 4 | 4 |
|  | 10 | 4 | 4 | 0 | 3 | 4 | 4 |
| 24 | 40 | 5 | 5 | 0 | 4 | 4 | 4 |
|  | 20 | 5 | 5 | 0 | 4 | 4 | 4 |
|  | 10 | 4 | 4 | 0 | 3 | 4 | 3 |
| 26 | 40 | 5 | 5 | 0 | 4 | 4 | 4 |
|  | 20 | 5 | 5 | 0 | 4 | 4 | 4 |
|  | 10 | 4 | 4 | 0 | 4 | 4 | 3 |
| 27 | 40 | 5 | 5 | 0 | 5 | 4 | 5 |
|  | 20 | 5 | 5 | 0 | 4 | 4 | 4 |
|  | 10 | 4 | 5 | 0 | 3 | 4 | 4 |
| 36 | 40 | 5 | 5 | 0 | 4 | 4 | 5 |
|  | 20 | 4 | 4 | 0 | 4 | 4 | 4 |
|  | 10 | 4 | 4 | 0 | 3 | 3 | 4 |
| 49 | 40 | 5 | 5 | 0 | 5 | 5 | 5 |
|  | 20 | 5 | 5 | 0 | 4 | 4 | 4 |
|  | 10 | 5 | 5 | 0 | 3 | 3 | 4 |
| 50 | 40 | 5 | 5 | 2 | 5 | 5 | 5 |
|  | 20 | 5 | 5 | 1 | 5 | 5 | 5 |
|  | 10 | 5 | 5 | 0 | 5 | 5 | 5 |
| 52 | 40 | 5 | 5 | 0 | 5 | 5 | 5 |
|  | 20 | 5 | 5 | 0 | 4 | 4 | 4 |
|  | 10 | 5 | 5 | 0 | 4 | 3 | 3 |
| 53 | 40 | 5 | 5 | 0 | 5 | 5 | 4 |
|  | 20 | 5 | 5 | 0 | 4 | 3 | 3 |
|  | 10 | 4 | 5 | 0 | 3 | 3 | 3 |
| 56 | 40 | 5 | 5 | 0 | 5 | 4 | 5 |
|  | 20 | 5 | 5 | 0 | 3 | 3 | 4 |
|  | 10 | 5 | 4 | 0 | 3 | 3 | 3 |
| 58 | 40 | 5 | 5 | 0 | 5 | 5 | 4 |
|  | 20 | 5 | 5 | 0 | 4 | 4 | 4 |
|  | 10 | 4 | 5 | 0 | 3 | 3 | 3 |
| 62 | 40 | 5 | 5 | 0 | 5 | 5 | 5 |
|  | 20 | 5 | 5 | 0 | 4 | 4 | 4 |
|  | 10 | 4 | 4 | 0 | 3 | 3 | 4 |
| 63 | 40 | 5 | 5 | 0 | 5 | 5 | 5 |
|  | 20 | 5 | 5 | 0 | 5 | 5 | 4 |
|  | 10 | 5 | 4 | 0 | 4 | 4 | 4 |
| 64 | 40 | 5 | 5 | 0 | 4 | 4 | 4 |
|  | 20 | 5 | 5 | 0 | 3 | 3 | 4 |
|  | 10 | 4 | 4 | 0 | 3 | 3 | 3 |
| 65 | 40 | 5 | 5 | 0 | 5 | 5 | 5 |
|  | 20 | 5 | 5 | 0 | 4 | 4 | 4 |
|  | 10 | 5 | 5 | 0 | 4 | 4 | 4 |
| 66 | 40 | 5 | 5 | 1 | 5 | 5 | 5 |
|  | 20 | 5 | 5 | 0 | 5 | 5 | 5 |
|  | 10 | 5 | 5 | 0 | 5 | 5 | 5 |
| 67 | 40 | 5 | 5 | 0 | 5 | 5 | 5 |
|  | 20 | 5 | 5 | 0 | 4 | 4 | 4 |
|  | 10 | 4 | 4 | 0 | 4 | 4 | 3 |
| 68 | 40 | 5 | 5 | 0 | 5 | 5 | 5 |
|  | 20 | 4 | 4 | 0 | 4 | 4 | 4 |
|  | 10 | 4 | 4 | 0 | 4 | 3 | 4 |
| 69 | 40 | 5 | 5 | 0 | 5 | 5 | 5 |
|  | 20 | 5 | 5 | 0 | 5 | 5 | 5 |
|  | 10 | 4 | 5 | 0 | 4 | 4 | 4 |
| 70 | 40 | 5 | 5 | 0 | 5 | 5 | 5 |
|  | 20 | 5 | 5 | 0 | 5 | 5 | 5 |
|  | 10 | 5 | 5 | 0 | 5 | 5 | 5 |
| 71 | 40 | 5 | 5 | 2 | 5 | 5 | 5 |
|  | 20 | 5 | 5 | 1 | 5 | 5 | 4 |
|  | 10 | 5 | 5 | 0 | 4 | 4 | 4 |
| 72 | 40 | 5 | 5 | 0 | 5 | 5 | 5 |
|  | 20 | 5 | 5 | 0 | 4 | 4 | 4 |
|  | 10 | 4 | 5 | 0 | 3 | 3 | 4 |

Table 1-continued

| Comp. No. | Amount applied (g./a.) | Barnyard grass | Large crab-grass | Radish | Redroot pigweed | Common purslane | Common lambs-quarter |
|---|---|---|---|---|---|---|---|
| 73 | 40 | 5 | 5 | 0 | 5 | 5 | 5 |
|  | 20 | 5 | 5 | 0 | 4 | 4 | 4 |
|  | 10 | 5 | 5 | 0 | 4 | 4 | 4 |
| 74 | 40 | 5 | 5 | 2 | 5 | 5 | 5 |
|  | 20 | 5 | 5 | 1 | 5 | 5 | 5 |
|  | 10 | 5 | 5 | 0 | 5 | 5 | 5 |
| 75 | 40 | 5 | 5 | 2 | 5 | 5 | 5 |
|  | 20 | 5 | 5 | 1 | 5 | 5 | 5 |
|  | 10 | 5 | 5 | 0 | 5 | 5 | 5 |
| 76 | 40 | 5 | 5 | 2 | 5 | 5 | 5 |
|  | 20 | 5 | 5 | 1 | 5 | 5 | 5 |
|  | 10 | 5 | 5 | 0 | 5 | 5 | 5 |
| 77 | 40 | 5 | 5 | 0 | 5 | 5 | 5 |
|  | 20 | 5 | 5 | 0 | 5 | 5 | 5 |
|  | 10 | 5 | 5 | 0 | 5 | 5 | 5 |
| 78 | 40 | 5 | 5 | 0 | 5 | 5 | 5 |
|  | 20 | 5 | 5 | 0 | 4 | 4 | 4 |
|  | 10 | 5 | 5 | 0 | 4 | 4 | 3 |
| 79 | 40 | 5 | 5 | 1 | 5 | 5 | 5 |
|  | 20 | 5 | 5 | 0 | 5 | 5 | 5 |
|  | 10 | 5 | 5 | 0 | 4 | 5 | 5 |
| 80 | 40 | 5 | 5 | 0 | 5 | 5 | 5 |
|  | 20 | 5 | 5 | 0 | 4 | 4 | 4 |
|  | 10 | 4 | 5 | 0 | 3 | 3 | 3 |
| 81 | 40 | 5 | 5 | 1 | 5 | 5 | 5 |
|  | 20 | 5 | 5 | 0 | 5 | 5 | 5 |
|  | 10 | 5 | 5 | 0 | 5 | 5 | 5 |
| 82 | 40 | 5 | 5 | 1 | 5 | 5 | 5 |
|  | 20 | 5 | 5 | 0 | 4 | 4 | 4 |
|  | 10 | 5 | 5 | 0 | 4 | 3 | 4 |
| 83 | 40 | 5 | 5 | 2 | 5 | 5 | 5 |
|  | 20 | 5 | 5 | 1 | 5 | 5 | 5 |
|  | 10 | 5 | 5 | 0 | 5 | 5 | 5 |
| 84 | 40 | 5 | 5 | 2 | 5 | 5 | 5 |
|  | 20 | 5 | 5 | 1 | 5 | 5 | 5 |
|  | 10 | 5 | 5 | 0 | 4 | 5 | 4 |
| 85 | 40 | 5 | 5 | 0 | 5 | 5 | 5 |
|  | 20 | 5 | 5 | 0 | 5 | 5 | 5 |
|  | 10 | 5 | 5 | 0 | 5 | 5 | 5 |
| 86 | 40 | 5 | 5 | 0 | 5 | 5 | 5 |
|  | 20 | 5 | 5 | 0 | 5 | 5 | 5 |
|  | 10 | 5 | 5 | 0 | 4 | 5 | 5 |
| 87 | 40 | 5 | 5 | 0 | 5 | 5 | 5 |
|  | 20 | 5 | 5 | 0 | 4 | 4 | 3 |
|  | 10 | 5 | 5 | 0 | 3 | 3 | 3 |
| 88 | 40 | 5 | 5 | 0 | 4 | 4 | 4 |
|  | 20 | 5 | 5 | 0 | 3 | 3 | 3 |
|  | 10 | 5 | 5 | 0 | 3 | 3 | 3 |
| 89 | 40 | 5 | 5 | 0 | 5 | 5 | 5 |
|  | 20 | 5 | 5 | 0 | 4 | 4 | 4 |
|  | 10 | 4 | 4 | 0 | 3 | 3 | 3 |
| 90 | 40 | 5 | 5 | 0 | 5 | 5 | 5 |
|  | 20 | 5 | 5 | 0 | 4 | 4 | 3 |
|  | 10 | 5 | 5 | 0 | 3 | 3 | 3 |
| 91 | 40 | 5 | 5 | 0 | 4 | 4 | 4 |
|  | 20 | 5 | 5 | 0 | 3 | 4 | 3 |
|  | 10 | 4 | 5 | 0 | 3 | 3 | 3 |
| 92 | 40 | 5 | 5 | 0 | 5 | 5 | 5 |
|  | 20 | 5 | 5 | 0 | 5 | 5 | 5 |
|  | 10 | 5 | 5 | 0 | 5 | 5 | 5 |
| 93 | 40 | 5 | 5 | 0 | 5 | 5 | 5 |
|  | 20 | 5 | 5 | 0 | 5 | 5 | 5 |
|  | 10 | 5 | 5 | 0 | 4 | 4 | 4 |
| 94 | 40 | 5 | 5 | 0 | 5 | 5 | 5 |
|  | 20 | 5 | 5 | 0 | 4 | 4 | 4 |
|  | 10 | 5 | 5 | 0 | 3 | 3 | 4 |
| 95 | 40 | 5 | 5 | 0 | 3 | 3 | 4 |
|  | 20 | 5 | 5 | 0 | 3 | 3 | 3 |
|  | 10 | 4 | 4 | 0 | 2 | 2 | 2 |
| 96 | 40 | 5 | 5 | 0 | 5 | 5 | 5 |
|  | 20 | 5 | 5 | 0 | 4 | 4 | 4 |
|  | 10 | 4 | 5 | 0 | 3 | 3 | 3 |
| 97 | 40 | 5 | 5 | 0 | 5 | 5 | 5 |
|  | 20 | 5 | 5 | 0 | 4 | 4 | 4 |
|  | 10 | 4 | 4 | 0 | 3 | 4 | 3 |
| 98 | 40 | 5 | 5 | 0 | 5 | 5 | 5 |
|  | 20 | 5 | 5 | 0 | 5 | 5 | 5 |
|  | 10 | 5 | 5 | 0 | 4 | 4 | 5 |
| 99 | 40 | 5 | 5 | 0 | 5 | 5 | 5 |
|  | 20 | 5 | 5 | 0 | 5 | 5 | 5 |
|  | 10 | 4 | 5 | 0 | 4 | 5 | 5 |
| 100 | 40 | 5 | 5 | 1 | 5 | 5 | 5 |
|  | 20 | 5 | 5 | 0 | 4 | 4 | 4 |
|  | 10 | 4 | 5 | 0 | 4 | 3 | 3 |
| PCP[1] (control) | 100 | 3 | 4 | 4 | 4 | 4 | 4 |
|  | 50 | 2 | 2 | 1 | 2 | 2 | 2 |
| Zytron[2] (control) | 40 | 4 | 3 | 0 | 1 | 2 | 2 |
|  | 20 | 3 | 1 | 0 | 0 | 1 | 0 |

Table 1-continued

| Comp. No. | Amount applied (g./a.) | Barnyard grass | Large crab-grass | Radish | Redroot pigweed | Common purslane | Common lambs-quarter |
| --- | --- | --- | --- | --- | --- | --- | --- |

Note:

[1] Chemical structure: pentachlorophenol (Cl₅C₆OH)

[2] Chemical structure: i-C₃H₇NH−P(=S)(OCH₃)−O−C₆H₃(Cl)₂ (with S, Cl substituents)

Test Example 2: Water application.

Wagner pots of 14 cm. in diameter, which had been packed with 1.5 kg. of paddy field soil, were brought into the state of paddy fields. To the pots were transplanted rice seedlings at the 3-leave stage. Further, seeds of barnyard grass (*Echinochloa crus-galli*) were sowed in the pots and required amounts of test compounds were applied to the soil under water lodged condition. 25 days after application, the degrees of herbicidal activity and phytotoxity were investigated on above-mentioned plants which had been transplanted and sowed, and on broad-leaved weeds, e.g., monochoria (*Monochoria viaginalis Presl.*), false pimpernel (*Linderna pyxidaria*) and toothcup (*Rotala indica Koehue*), which had been spontaneously germinated. The test compounds were used in the form of wettable powder. The results obtained are as shown in Table 2. The herbicidal effects and the phytotoxity were evaluated as follows by the numerals ranging from 0 to 5.

| | Effect on plants |
| --- | --- |
| 0 | no effect |
| 1 | very slightly affected |
| 2 | slightly affected |
| 3 | moderately affected |
| 4 | considerably affected |
| 5 | completely killed |

Table 2

| Compound No. | Amount applied (g/a) | Herbicidal effects – Barnyard grass | Herbicidal effects – Broad-leaved weeds | Phytotoxicity on rice |
| --- | --- | --- | --- | --- |
| 1 | 40 | 5 | 5 | 0 |
|   | 20 | 5 | 5 | 0 |
|   | 10 | 5 | 5 | 0 |
| 2 | 40 | 5 | 5 | 1 |
|   | 20 | 5 | 5 | 1 |
|   | 10 | 5 | 5 | 0 |
| 3 | 40 | 5 | 5 | 0 |
|   | 20 | 5 | 5 | 0 |
|   | 10 | 5 | 5 | 0 |
| 4 | 40 | 5 | 5 | 0 |
|   | 20 | 5 | 5 | 0 |
|   | 10 | 5 | 4 | 0 |
| 5 | 40 | 5 | 5 | 0 |
|   | 20 | 5 | 5 | 0 |
|   | 10 | 5 | 5 | 0 |
| 7 | 40 | 5 | 5 | 0 |
|   | 20 | 5 | 5 | 0 |
|   | 10 | 5 | 5 | 0 |
| 8 | 40 | 5 | 5 | 0 |
|   | 20 | 5 | 5 | 0 |
|   | 10 | 5 | 4 | 0 |
| 9 | 40 | 5 | 5 | 0 |
|   | 20 | 5 | 5 | 0 |
|   | 10 | 5 | 5 | 0 |
| 10 | 40 | 5 | 5 | 0 |
|   | 20 | 5 | 5 | 0 |
|   | 10 | 5 | 4 | 0 |
| 11 | 40 | 5 | 5 | 0 |
|   | 20 | 5 | 5 | 0 |
|   | 10 | 5 | 5 | 0 |
| 12 | 40 | 5 | 5 | 0 |
|   | 20 | 5 | 5 | 0 |
|   | 10 | 5 | 5 | 0 |
| 13 | 40 | 5 | 5 | 0 |
|   | 20 | 5 | 5 | 0 |
|   | 10 | 5 | 5 | 0 |
| 14 | 40 | 5 | 5 | 0 |
|   | 20 | 5 | 5 | 0 |
|   | 10 | 5 | 5 | 0 |
| 15 | 40 | 5 | 5 | 0 |
|   | 20 | 5 | 5 | 0 |
|   | 10 | 5 | 5 | 0 |
| 16 | 40 | 5 | 5 | 0 |
|   | 20 | 5 | 5 | 0 |
|   | 10 | 5 | 5 | 0 |
| 17 | 40 | 5 | 5 | 0 |
|   | 20 | 5 | 5 | 0 |
|   | 10 | 5 | 4 | 0 |
| 18 | 40 | 5 | 5 | 0 |
|   | 20 | 5 | 5 | 0 |
|   | 10 | 5 | 5 | 0 |
| 19 | 40 | 5 | 5 | 0 |
|   | 20 | 5 | 5 | 0 |
|   | 10 | 5 | 4 | 0 |
| 22 | 40 | 5 | 5 | 0 |
|   | 20 | 5 | 5 | 0 |
|   | 10 | 5 | 5 | 0 |
| 24 | 40 | 5 | 5 | 0 |
|   | 20 | 5 | 5 | 0 |
|   | 10 | 5 | 4 | 0 |
| 26 | 40 | 5 | 5 | 0 |
|   | 20 | 5 | 5 | 0 |
|   | 10 | 5 | 5 | 0 |
| 27 | 40 | 5 | 5 | 0 |
|   | 20 | 5 | 5 | 0 |
|   | 10 | 5 | 5 | 0 |
| 36 | 40 | 5 | 5 | 1 |
|   | 20 | 5 | 5 | 0 |
|   | 10 | 5 | 4 | 0 |
| 49 | 40 | 5 | 5 | 1 |
|   | 20 | 5 | 5 | 0 |
|   | 10 | 5 | 5 | 0 |
| 50 | 40 | 5 | 5 | 0 |
|   | 20 | 5 | 5 | 0 |
|   | 10 | 5 | 5 | 0 |
| 52 | 40 | 5 | 5 | 0 |
|   | 20 | 5 | 5 | 0 |
|   | 10 | 5 | 5 | 0 |
| 53 | 40 | 5 | 5 | 0 |
|   | 20 | 5 | 5 | 0 |
|   | 10 | 5 | 5 | 0 |
| 56 | 40 | 5 | 5 | 0 |
|   | 20 | 5 | 5 | 0 |
|   | 10 | 5 | 5 | 0 |

Table 2-continued

| Compound No. | Amount applied (g/a) | Herbicidal effects Barnyard grass | Herbicidal effects Broad-leaved weeds | Phytotoxicity on rice |
|---|---|---|---|---|
| 58 | 20 | 5 | 5 | 0 |
|  | 10 | 5 | 5 | 0 |
| 62 | 40 | 5 | 5 | 0 |
|  | 20 | 5 | 5 | 0 |
|  | 10 | 5 | 5 | 0 |
| 63 | 40 | 5 | 5 | 0 |
|  | 20 | 5 | 5 | 0 |
|  | 10 | 4 | 5 | 0 |
| 64 | 40 | 5 | 5 | 0 |
|  | 20 | 5 | 5 | 0 |
|  | 10 | 5 | 5 | 0 |
| 65 | 40 | 5 | 5 | 0 |
|  | 20 | 5 | 5 | 0 |
|  | 10 | 4 | 5 | 0 |
| 66 | 40 | 5 | 5 | 0 |
|  | 20 | 5 | 5 | 0 |
|  | 10 | 5 | 5 | 0 |
| 67 | 40 | 5 | 5 | 0 |
|  | 20 | 5 | 5 | 0 |
|  | 10 | 5 | 5 | 0 |
| 68 | 40 | 5 | 5 | 0 |
|  | 20 | 5 | 5 | 0 |
|  | 10 | 5 | 5 | 0 |
| 69 | 40 | 5 | 5 | 1 |
|  | 20 | 5 | 5 | 0 |
|  | 10 | 5 | 5 | 0 |
| 70 | 40 | 5 | 5 | 2 |
|  | 20 | 5 | 5 | 0 |
|  | 10 | 5 | 5 | 0 |
| 71 | 40 | 5 | 5 | 0 |
|  | 20 | 5 | 5 | 0 |
|  | 10 | 5 | 5 | 0 |
| 72 | 40 | 5 | 5 | 0 |
|  | 20 | 5 | 5 | 0 |
|  | 10 | 5 | 5 | 0 |
| 73 | 40 | 5 | 5 | 0 |
|  | 20 | 5 | 5 | 0 |
|  | 10 | 5 | 5 | 0 |
| 74 | 40 | 5 | 5 | 0 |
|  | 20 | 5 | 5 | 0 |
|  | 10 | 5 | 5 | 0 |
| 75 | 40 | 5 | 5 | 1 |
|  | 20 | 5 | 5 | 0 |
|  | 10 | 5 | 5 | 0 |
| 76 | 40 | 5 | 5 | 0 |
|  | 20 | 5 | 5 | 0 |
|  | 10 | 5 | 5 | 0 |
| 77 | 40 | 5 | 5 | 1 |
|  | 20 | 5 | 5 | 0 |
|  | 10 | 5 | 5 | 0 |
| 78 | 40 | 5 | 5 | 0 |
|  | 20 | 5 | 5 | 0 |
|  | 10 | 5 | 5 | 0 |
| 79 | 40 | 5 | 5 | 1 |
|  | 20 | 5 | 5 | 0 |
|  | 10 | 5 | 5 | 0 |
| 80 | 40 | 5 | 5 | 2 |
|  | 20 | 5 | 5 | 0 |
|  | 10 | 4 | 5 | 0 |
| 81 | 40 | 5 | 5 | 1 |
|  | 20 | 5 | 5 | 0 |
|  | 10 | 5 | 5 | 0 |
| 82 | 40 | 5 | 5 | 2 |
|  | 20 | 5 | 5 | 0 |
|  | 10 | 5 | 5 | 0 |
| 83 | 40 | 5 | 5 | 0 |
|  | 20 | 5 | 5 | 0 |
|  | 10 | 5 | 5 | 0 |
| 84 | 40 | 5 | 5 | 2 |
|  | 20 | 5 | 5 | 0 |
|  | 10 | 5 | 5 | 0 |
| 85 | 40 | 5 | 5 | 0 |
|  | 20 | 5 | 5 | 0 |
|  | 10 | 5 | 5 | 0 |
| 86 | 40 | 5 | 5 | 0 |
|  | 20 | 5 | 5 | 0 |
|  | 10 | 5 | 5 | 0 |
| 87 | 40 | 5 | 5 | 0 |
|  | 20 | 5 | 5 | 0 |
|  | 10 | 5 | 5 | 0 |
| 88 | 40 | 5 | 5 | 0 |
|  | 20 | 5 | 5 | 0 |
|  | 10 | 5 | 5 | 0 |
| 89 | 40 | 5 | 5 | 0 |
|  | 20 | 5 | 5 | 0 |
|  | 10 | 5 | 5 | 0 |
| 90 | 40 | 5 | 5 | 1 |
|  | 20 | 5 | 5 | 0 |
|  | 10 | 5 | 5 | 0 |
| 91 | 40 | 5 | 5 | 0 |
|  | 20 | 5 | 5 | 0 |
|  | 10 | 4 | 5 | 0 |
| 92 | 40 | 5 | 5 | 2 |
|  | 20 | 5 | 5 | 0 |
|  | 10 | 5 | 5 | 0 |
| 93 | 40 | 5 | 5 | 0 |
|  | 20 | 5 | 5 | 0 |
|  | 10 | 5 | 5 | 0 |
| 94 | 40 | 5 | 5 | 0 |
|  | 20 | 5 | 5 | 0 |
|  | 10 | 5 | 5 | 0 |
| 95 | 40 | 5 | 5 | 0 |
|  | 20 | 5 | 5 | 0 |
|  | 10 | 5 | 5 | 0 |
| 96 | 40 | 5 | 5 | 0 |
|  | 20 | 5 | 5 | 0 |
|  | 10 | 5 | 5 | 0 |
| 97 | 40 | 5 | 5 | 0 |
|  | 20 | 5 | 5 | 0 |
|  | 10 | 5 | 5 | 0 |
| 98 | 40 | 5 | 5 | 0 |
|  | 20 | 5 | 5 | 0 |
|  | 10 | 5 | 5 | 0 |
| 99 | 40 | 5 | 5 | 0 |
|  | 20 | 5 | 5 | 0 |
|  | 10 | 5 | 5 | 0 |
| 100 | 40 | 5 | 5 | 0 |
|  | 20 | 5 | 5 | 0 |
|  | 10 | 5 | 5 | 0 |
| PCP (control) | 100 | 5 | 5 | 3 |
|  | 50 | 4 | 5 | 2 |
| Zytron (control) | 40 | 3 | 3 | 0 |
|  | 20 | 1 | 2 | 0 |
| NIP[1] (control) | 40 | 5 | 5 | 4 |
|  | 20 | 5 | 5 | 2 |

Note:

[1]Chemical structure

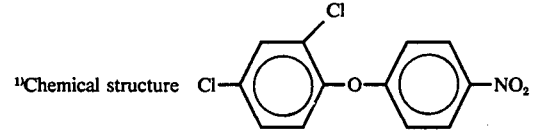

Test Example 3

Lethal effect on carmine mite (Tetranychus telavius)

A large number of carmine mite adult were made parasitic on leaves of potted kidney beans at a 2-leaves stage which had elapsed 10 days after sowing. The leaves of kidney bean on which carmine mites had been made parasitic were dipped for 1 minute in each aqueous solution of the present compounds of wettable powder type. Water was given to the leaves not to kill them, and after 48 hours the death and alive were observed microscopically to calculate the mortality. Values of $LC_{50}$ were obtained from the mortality. The results are as shown in Table 3.

Table 3

| Compound No. | $LC_{50}$ (p.p.m.) |
|---|---|
| 2 | 4.6 |
| 3 | 18.5 |
| 4 | 11.4 |
| 5 | 7.9 |
| 7 | 18.5 |
| 11 | 50.0 |
| 14 | 23.1 |
| 30 | 22.8 |
| Smite[1] (control) | 102.0 |

[1]Chemical structure:

Table 3-continued

| Compound No. | LC$_{50}$ (p.p.m.) |
|---|---| t-C$_4$H$_9$—⟨phenyl⟩—OCH$_2$CHOCH$_2$CHOSOCH$_2$Cl
　　　　　　　　　　|　　　　　|
　　　　　　　　　　CH$_3$　　CH$_3$ (with O double-bonded to S)

Test Example 4

Lethal effect on carmine mite (Tetranychus telarius)

About 50 carmine mite adults were made parasitic on leaves of potted kidney beans at a 2-leaves stage which had elapsed 10 days after swing. After a week, the present compounds of a 25% wettable powder type were each applied in the form of a 200 fold dilute solution. After allowing to stand for another week the degree of damage was observed, the results of which are as shown in Table 4.

Table 4

| Compound No. | Degree of damage |
|---|---|
| 49 | − |
| 53 | −~+ |
| 60 | − |
| 61 | − |
| No treatment | +++ |

Note:
−: damage is hardly increased.
+: damage is slightly increased.
++: damage is fairly increased.
+++: damage is heavily increased.

Test Example 5

Lethal effect on tobacco cut work (Spondoptera litura)

The present compounds of an emulsifiable concentrate type were applied to leaves of chinese cabbage in the form of an 1000 fold dilute solution. After air-drying, third to fourth instar larvae of tobacco cut worm were released and after 48 hours the death and alive were observed. The results are as shown in Table 5.

Table 5

| Compound No. | Mortality (%) |
|---|---|
| 2 | 100 |
| 3 | 83.3 |
| 5 | 70.0 |
| 13 | 73.3 |
| 49 | 75.0 |
| 50 | 81.2 |
| 58 | 72.0 |
| EPN[1] (control) | 70.0 |

[1]Chemical structure:

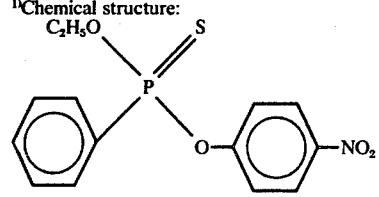

Test Example 6

Lethal effect on rice stem borer (Chilo suppressalis)

Eggs just before hatch of the rice stem borer were applied in a ratio of 100/pot near the root of rice plants grown up into the tillering stage in an 1/1000000 Wagner's pot. After eggs were hatched and the larvae entered into stems of rice plants, an 1000 fold dilute solution of each 50 % emulsifiable concentrates of the present compounds was applied by means of a turn table. The death and alive were observed to calculate the mortality 4 days after application. The results are as shown in Table 6.

Table 6

| Compound No. | Mortality (%) |
|---|---|
| 4 | 97.6 |
| 5 | 88.9 |
| 6 | 75.0 |
| 9 | 100 |
| 18 | 76.4 |
| 24 | 83.0 |
| 31 | 69.5 |
| 35 | 95.0 |
| Malathion[1] (control) | 41.3 |

[1]Chemical structure:

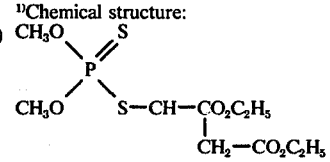

Test Example 7

Effect on nematode 0.5 ml. of a nematode-containing aqueous solution separated from food according to Baermann's method was placed in a test tube with ground stopper containing 0.5 ml. of an aqueous dilute solution of each emulsifiable concentrates of the present compounds. The concentration of the active ingredient in the mixture was adjusted to 500 p.p.m. After 24 hours, the death and alive were observed microscopically to calculate the mortality. The results are as shown in Table 7.

Table 7

| Compound No. | Mortality (%) |
|---|---|
| 2 | 100 |
| 3 | 100 |
| 4 | 100 |
| 5 | 100 |
| 7 | 100 |
| 9 | 100 |
| 10 | 100 |
| 11 | 100 |
| 12 | 100 |
| 14 | 100 |
| 28 | 100 |
| 33 | 100 |
| 49 | 100 |
| 50 | 100 |
| 52 | 85.7 |
| 53 | 83.6 |
| 57 | 91.0 |
| Dichloropropene[1] (control) | 79.3 |

[1]Chemical structure: ClCH=C—CH$_2$Cl

Test Example 8

Lethal effect on tobacco cut worm (Spodoptera litura) and diamond-back moth (Plutella maculipennis)

A 3% dust of each compound of the present invention was applied, in a proportion of 5 kg./10 a., to the field of cabbage where a large number of tobacco cut worm and diamond-back moth were generated, After 7 days, 20 cabbages were pulled out and the number of insects thereon were checked. The results are as shown in Table 8.

Table 8

| Compound No. | Number of insects | |
|---|---|---|
| | Tobacco cut worm | Diamond-back moth |
| 2 | 0 | 8 |
| 3 | 1 | 12 |
| No treatment | 47 | 158 |
| Bipterex[1] (control) | 19 | 49 |

[1]Chemical structure:

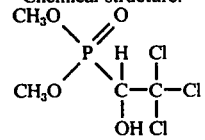

The treated cabbages suffered only the same feeding damage as before dusting, however with the untreated cabbages only leaf veins were left.

The synthetic method according to the present invention will be illustrated with reference to the following examples which are only illustrative but not limitative thereto.

EXAMPLE 1

(Compound No. 2)

To a solution of 26.2 g. of potassium O-ethyl-S-n-propylphosphorodithioate in 100 ml. of ethylalcohol, were added 17.5 g of 2-methylpiperidino-α-chloroacetamide, and then the mixture was refluxed under stirring for 2 hours. After removal of ethylalcohol under reduced pressure, the remainder was dissolved in benzene. The resulting solution was washed with a 5% sodium carbonate solution and then water. Thereafter benzene was distilled off to obtain 29.7 g. of pale yellow and oily O-ethyl-S-n-propyl-S(2-methyl-piperidinocarbomoylmethyl)phosphorodithiolate ($n_D^{23.0}$ 1.5320).

| Elementary analysis: | | |
|---|---|---|
| Calculated (%) (as $C_{13}H_{26}NO_3PS_2$) | | Found (%) |
| P | 9.12 | 8.97 |
| C | 46.00 | 45.91 |
| H | 7.72 | 7.81 |
| N | 4.13 | 4.14 |

EXAMPLE 2

(Compound No. 16)

To a solution of 26.0 g. of sodium O-n-propyl-S-n-propylphosphorodithioate in 100 ml. of acetone, were added 17.5 g. of 2-methylpiperidino-α-α-chloroacetoamide, and then the mixture was refluxed under stirring for 2 hours, and thereafter treated in the same manner as described in Example 1. 29.6 g. of pale yellow and oily O,S-di-n-propyl-S-(2-methylpiperidinocarbamoyl-methyl)phosphorodithiolate ($n_D^{27.0}$ 1.5224) were obtained.

| Elementary analysis: | | |
|---|---|---|
| Calculated (%) (as $C_{14}H_{28}NO_3PS_2$) | | Found (%) |
| P | 8.76 | 8.81 |
| C | 47.57 | 47.36 |
| H | 7.98 | 7.87 |
| N | 3.96 | 3.78 |

EXAMPLE 3

(Compound No. 49)

To a solution of 35.0 g. of potassium O-ethyl-S-(4-chlorobenzyl)-phosphorodithioate in 100 ml. of ethanol, were added 17.5 g. of 2-methylpiperidino-α-chloroacetamide. The mixture was refluxed under stirring for 2 hours. After removal of ethanol under reduced pressure, the remainder was dissolved in benzene. The resulting solution was washed with a 5% sodium carbonate solution and then water. Thereafter benzene was distilled off to obtain 34.2 g. of yellow and oily O-ethyl-S-(4-chlorobenzyl)-S-(2-methyl-piperidinocarbamoylmethyl)phosphorodithiolate ($n_D^{20.0}$ 1.5680).

| Elementary analysis: | | |
|---|---|---|
| Calculated (%) (as $C_{17}H_{25}ClNO_3PS_2$) | | Found (%) |
| C | 48.39 | 48.28 |
| H | 5.97 | 5.98 |
| N | 3.32 | 3.39 |
| P | 7.34 | 7.25 |

| Ex. No. | Compound No. | Yield (%) | Refractive index | | Elementary analysis Calculated (%) | Found (%) |
|---|---|---|---|---|---|---|
| 4 | 1 | 86.2 | $n_D^{26.5}$ 1.5330 | C | 44.29 | 44.51 |
| | | | | H | 7.43 | 7.29 |
| | | | | N | 4.30 | 4.27 |
| | | | | P | 9.52 | 9.38 |
| 5 | 3 | 89.1 | $n_D^{24.0}$ 1.5309 | C | 46.00 | 45.71 |
| | | | | H | 7.72 | 7.72 |
| | | | | N | 4.13 | 4.25 |
| | | | | P | 9.12 | 9.07 |
| 6 | 4 | 84.2 | $n_D^{24.0}$ 1.5281 | C | 47.57 | 47.34 |
| | | | | H | 7.98 | 8.15 |
| | | | | N | 3.96 | 3.99 |
| | | | | P | 8.76 | 8.98 |
| 7 | 5 | 91.9 | $n_D^{24.0}$ 1.5287 | C | 47.57 | 47.80 |
| | | | | H | 7.98 | 7.96 |
| | | | | N | 3.96 | 3.97 |
| | | | | P | 8.76 | 8.81 |
| 8 | 6 | 87.7 | $n_D^{25.0}$ 1.5284 | C | 47.57 | 47.35 |
| | | | | H | 7.98 | 8.07 |
| | | | | N | 3.96 | 3.86 |
| | | | | P | 8.76 | 8.97 |
| 9 | 7 | 88.0 | $n_D^{24.0}$ 1.5242 | C | 49.02 | 48.68 |
| | | | | H | 8.23 | 8.30 |
| | | | | N | 3.81 | 3.82 |
| | | | | P | 8.43 | 8.73 |
| 10 | 8 | 88.0 | $n_D^{26.5}$ 1.5160 | C | 52.78 | 52.51 |
| | | | | H | 8.86 | 8.96 |
| | | | | N | 3.42 | 3.41 |
| | | | | P | 7.56 | 7.85 |
| 11 | 9 | 89.7 | $n_D^{25.0}$ 1.5412 | C | 41.99 | 42.23 |
| | | | | H | 6.23 | 6.51 |
| | | | | N | 3.71 | 4.00 |
| | | | | P | 8.33 | 8.71 |
| 12 | 10 | 79.5 | $n_D^{25.0}$ 1.5395 | C | 50.64 | 50.32 |
| | | | | H | 7.97 | 7.76 |
| | | | | N | 3.69 | 3.77 |

| Ex. No. | Compound No. | Yield (%) | Refractive index | Elementary analysis Calculated (%) | | Found (%) |
|---|---|---|---|---|---|---|
|  |  |  |  | P | 8.16 | 8.41 |
|  |  |  |  | C | 52.69 | 52.87 |
|  |  |  |  | H | 6.76 | 6.87 |
| 13 | 11 | 85.7 | $n_D^{28.0}$ 1.5652 |  |  |  |
|  |  |  |  | N | 3.61 | 3.53 |
|  |  |  |  | P | 7.99 | 8.13 |
|  |  |  |  | C | 45.99 | 45.71 |
|  |  |  |  | H | 7.72 | 7.83 |
| 14 | 12 | 85.9 | $n_D^{28.0}$ 1.5270 |  |  |  |
|  |  |  |  | N | 4.13 | 4.01 |
|  |  |  |  | P | 9.12 | 8.87 |
|  |  |  |  | C | 45.99 | 46.23 |
|  |  |  |  | H | 7.72 | 7.50 |
| 15 | 13 | 87.8 | $n_D^{25.0}$ 1.5287 |  |  |  |
|  |  |  |  | N | 4.13 | 4.11 |
|  |  |  |  | P | 9.12 | 9.41 |
|  |  |  |  | C | 47.57 | 47.63 |
|  |  |  |  | H | 7.98 | 7.84 |
| 16 | 14 | 92.9 | $n_D^{25.0}$ 1.5266 |  |  |  |
|  |  |  |  | N | 3.96 | 3.83 |
|  |  |  |  | P | 8.76 | 8.78 |
|  |  |  |  | C | 47.57 | 47.36 |
|  |  |  |  | H | 7.98 | 7.89 |
| 17 | 15 | 80.9 | $n_D^{25.0}$ 1.5270 |  |  |  |
|  |  |  |  | N | 3.96 | 3.88 |
|  |  |  |  | P | 8.76 | 9.03 |
|  |  |  |  | C | 49.02 | 49.37 |
|  |  |  |  | H | 8.23 | 8.21 |
| 18 | 17 | 85.0 | $n_D^{27.0}$ 1.5211 |  |  |  |
|  |  |  |  | N | 3.81 | 3.76 |
|  |  |  |  | P | 8.43 | 8.10 |
|  |  |  |  | C | 44.02 | 44.31 |
|  |  |  |  | H | 8.00 | 7.88 |
| 19 | 18 | 85.7 | $n_D^{26.5}$ 1.5301 |  |  |  |
|  |  |  |  | N | 4.28 | 4.21 |
|  |  |  |  | P | 9.46 | 9.62 |
|  |  |  |  | C | 55.92 | 56.13 |
|  |  |  |  | H | 7.51 | 7.27 |
| 20 | 19 | 78.1 | $n_D^{27.0}$ 1.5541 |  |  |  |
|  |  |  |  | N | 3.26 | 3.24 |
|  |  |  |  | P | 7.21 | 7.53 |
|  |  |  |  | C | 47.57 | 47.39 |
|  |  |  |  | H | 7.98 | 7.81 |
| 21 | 20 | 70.5 | $n_D^{24.5}$ 1.5220 |  |  |  |
|  |  |  |  | N | 3.96 | 3.92 |
|  |  |  |  | P | 8.76 | 8.95 |
|  |  |  |  | C | 47.57 | 47.86 |
|  |  |  |  | H | 7.98 | 8.15 |
| 22 | 21 | 73.5 | $n_D^{27.0}$ 1.5245 |  |  |  |
|  |  |  |  | N | 3.96 | 3.82 |
|  |  |  |  | P | 8.76 | 8.51 |
|  |  |  |  | C | 46.00 | 45.71 |
|  |  |  |  | H | 7.72 | 7.96 |
| 23 | 22 | 87.6 | $n_D^{28.0}$ 1.5255 |  |  |  |
|  |  |  |  | N | 4.13 | 4.07 |
|  |  |  |  | P | 9.12 | 9.37 |
|  |  |  |  | C | 47.57 | 47.28 |
|  |  |  |  | H | 7.98 | 8.13 |
| 24 | 23 | 74.0 | $n_D^{27.0}$ 1.5249 |  |  |  |
|  |  |  |  | N | 3.96 | 3.87 |
|  |  |  |  | P | 8.76 | 9.01 |
|  |  |  |  | C | 47.57 | 47.29 |
|  |  |  |  | H | 7.98 | 8.03 |
| 25 | 24 | 93.5 | $n_D^{28.0}$ 1.5216 |  |  |  |
|  |  |  |  | N | 3.96 | 4.11 |
|  |  |  |  | P | 8.76 | 8.68 |
|  |  |  |  | C | 47.57 | 47.87 |
|  |  |  |  | H | 7.98 | 7.76 |
| 26 | 25 | 89.0 | $n_D^{27.0}$ 1.5248 |  |  |  |
|  |  |  |  | N | 3.96 | 3.88 |
|  |  |  |  | P | 8.76 | 8.56 |
|  |  |  |  | C | 46.00 | 46.25 |
|  |  |  |  | H | 7.72 | 7.84 |
| 27 | 26 | 87.5 | $n_D^{28.0}$ 1.5240 |  |  |  |
|  |  |  |  | N | 4.13 | 4.21 |
|  |  |  |  | P | 9.12 | 9.03 |
|  |  |  |  | C | 47.57 | 47.73 |
|  |  |  |  | H | 7.98 | 8.11 |
| 28 | 27 | 80.0 | $n_D^{28.0}$ 1.5205 |  |  |  |
|  |  |  |  | N | 3.96 | 4.11 |
|  |  |  |  | P | 8.76 | 8.52 |
|  |  |  |  | C | 47.57 | 47.54 |
|  |  |  |  | H | 7.98 | 8.07 |
| 29 | 44 | 82.9 | $n_D^{25.0}$ 1.5272 |  |  |  |
|  |  |  |  | N | 3.96 | 3.89 |
|  |  |  |  | P | 8.76 | 8.86 |
|  |  |  |  | C | 49.02 | 49.31 |
|  |  |  |  | H | 8.23 | 8.42 |
| 30 | 45 | 86.5 | $n_D^{27.0}$ 1.5224 |  |  |  |
|  |  |  |  | N | 3.81 | 3.76 |
|  |  |  |  | P | 8.43 | 8.27 |
|  |  |  |  | C | 49.02 | 50.27 |
|  |  |  |  | H | 8.23 | 8.00 |
| 31 | 46 | 83.6 | $n_D^{25.0}$ 1.5230 |  |  |  |
|  |  |  |  | N | 3.81 | 3.68 |
|  |  |  |  | P | 8.43 | 8.71 |
|  |  |  |  | C | 49.02 | 48.87 |
|  |  |  |  | H | 8.23 | 8.15 |
| 32 | 47 | 82.1 | $n_D^{27.0}$ 1.5255 |  |  |  |
|  |  |  |  | N | 3.81 | 3.78 |
|  |  |  |  | P | 8.43 | 8.29 |
|  |  |  |  | C | 49.02 | 49.16 |
|  |  |  |  | H | 8.23 | 8.35 |
| 33 | 48 | 75.0 | $n_D^{25.0}$ 1.5223 |  |  |  |
|  |  |  |  | N | 3.81 | 3.91 |
|  |  |  |  | P | 8.43 | 8.36 |
|  |  |  |  | C | 56.85 | 56.92 |
|  |  |  |  | H | 7.44 | 7.71 |
| 34 | 50 | 81.3 | $n_D^{22.0}$ 1.5592 |  |  |  |
|  |  |  |  | N | 3.16 | 3.22 |
|  |  |  |  | P | 6.98 | 6.63 |
|  |  |  |  | C | 49.59 | 49.36 |
|  |  |  |  | H | 6.24 | 6.29 |
| 35 | 51 | 82.4 | $n_D^{21.0}$ 1.5636 |  |  |  |
|  |  |  |  | N | 3.21 | 3.35 |
|  |  |  |  | P | 7.10 | 7.03 |
|  |  |  |  | C | 53.84 | 53.62 |
|  |  |  |  | H | 7.04 | 7.00 |
| 36 | 52 | 80.5 | $n_D^{23.0}$ 1.5700 |  |  |  |
|  |  |  |  | N | 3.49 | 3.45 |
|  |  |  |  | P | 7.71 | 7.57 |
|  |  |  |  | C | 54.91 | 54.88 |
|  |  |  |  | H | 7.29 | 6.91 |
| 37 | 53 | 80.9 | $n_D^{23.0}$ 1.5652 |  |  |  |
|  |  |  |  | N | 3.37 | 3.56 |
|  |  |  |  | P | 7.45 | 7.20 |
|  |  |  |  | C | 55.91 | 55.92 |
|  |  |  |  | H | 7.52 | 7.51 |
| 38 | 56 | 81.2 | $n_D^{18.0}$ 1.5600 |  |  |  |
|  |  |  |  | N | 3.26 | 3.21 |
|  |  |  |  | P | 7.21 | 7.21 |
|  |  |  |  | C | 55.92 | 56.07 |
|  |  |  |  | H | 7.51 | 7.37 |
| 39 | 58 | 83.1 | $n_D^{21.0}$ 1.5608 |  |  |  |
|  |  |  |  | N | 3.26 | 3.29 |
|  |  |  |  | P | 7.21 | 7.41 |
|  |  |  |  | C | 50.86 | 50.58 |
|  |  |  |  | H | 8.47 | 8.25 |
| 40 | 62 | 82.7 | $n_D^{18.0}$ 1.5261 |  |  |  |
|  |  |  |  | N | 3.67 | 3.62 |
|  |  |  |  | P | 8.12 | 7.91 |
|  |  |  |  | C | 53.84 | 52.29 |
|  |  |  |  | H | 7.04 | 7.06 |
| 41 | 63 | 83.4 | $n_D^{20.0}$ 1.5649 |  |  |  |
|  |  |  |  | N | 3.50 | 3.61 |
|  |  |  |  | P | 7.71 | 7.69 |
|  |  |  |  | C | 53.84 | 53.87 |
|  |  |  |  | H | 7.04 | 7.10 |
| 42 | 64 | 84.1 | $n_D^{20.0}$ 1.5685 |  |  |  |
|  |  |  |  | N | 3.49 | 3.54 |
|  |  |  |  | P | 7.71 | 7.65 |
|  |  |  |  | C | 54.91 | 54.65 |
|  |  |  |  | H | 7.29 | 7.31 |
| 43 | 65 | 81.9 | $n_D^{22.5}$ 1.5629 |  |  |  |
|  |  |  |  | N | 3.37 | 3.35 |
|  |  |  |  | P | 7.45 | 7.18 |
|  |  |  |  | C | 44.28 | 44.34 |
|  |  |  |  | H | 7.45 | 7.46 |
| 44 | 66 | 82.2 | $n_D^{21.0}$ 1.5388 |  |  |  |
|  |  |  |  | N | 4.30 | 4.37 |
|  |  |  |  | P | 9.52 | 9.47 |
|  |  |  |  | C | 49.01 | 49.62 |
|  |  |  |  | H | 8.24 | 8.26 |
| 45 | 67 | 82.4 | $n_D^{21.5}$ 1.5276 |  |  |  |
|  |  |  |  | N | 3.81 | 4.03 |
|  |  |  |  | P | 8.43 | 8.21 |
|  |  |  |  | C | 50.36 | 50.22 |
|  |  |  |  | H | 8.48 | 8.49 |
| 46 | 68 | 79.8 | $n_D^{21.0}$ 1.5243 |  |  |  |
|  |  |  |  | N | 3.67 | 3.66 |
|  |  |  |  | P | 8.12 | 7.92 |
|  |  |  |  | C | 50.36 | 50.43 |
|  |  |  |  | H | 8.47 | 8.48 |
| 47 | 69 | 81.2 | $n_D^{28.0}$ 1.5247 |  |  |  |
|  |  |  |  | N | 3.67 | 3.68 |
|  |  |  |  | P | 8.12 | 8.17 |

| Ex. No. | Compound No. | Yield (%) | Refractive index | Elementary analysis | Calculated (%) | Found (%) |
|---|---|---|---|---|---|---|
| 48 | 70 | 80.5 | $n_D^{23.5}$ 1.5391 | C | 47.83 | 47.82 |
|  |  |  |  | H | 7.47 | 7.54 |
|  |  |  |  | N | 3.99 | 4.09 |
|  |  |  |  | P | 8.81 | 8.36 |
| 49 | 71 | 82.1 | $n_D^{28.0}$ 1.5360 | C | 44.28 | 44.22 |
|  |  |  |  | H | 7.45 | 7.56 |
|  |  |  |  | N | 4.30 | 4.39 |
|  |  |  |  | P | 9.52 | 9.67 |
| 50 | 72 | 83.4 | $n_D^{22.5}$ 1.5258 | C | 49.01 | 49.10 |
|  |  |  |  | H | 8.24 | 8.28 |
|  |  |  |  | N | 3.81 | 3.84 |
|  |  |  |  | P | 8.43 | 8.20 |
| 51 | 73 | 82.5 | $n_D^{20.5}$ 1.5260 | C | 49.01 | 49.01 |
|  |  |  |  | H | 8.24 | 8.18 |
|  |  |  |  | N | 3.81 | 3.95 |
|  |  |  |  | P | 8.43 | 8.71 |
| 52 | 74 | 82.9 | $n_D^{23.0}$ 1.5409 | C | 44.28 | 44.43 |
|  |  |  |  | H | 7.45 | 7.67 |
|  |  |  |  | N | 4.30 | 4.51 |
|  |  |  |  | P | 9.52 | 9.47 |
| 53 | 75 | 82.7 | $n_D^{22.0}$ 1.5338 | C | 45.99 | 46.12 |
|  |  |  |  | H | 7.74 | 7.89 |
|  |  |  |  | N | 4.13 | 4.19 |
|  |  |  |  | P | 9.12 | 8.97 |
| 54 | 76 | 82.5 | $n_D^{22.5}$ 1.5298 | C | 47.56 | 47.61 |
|  |  |  |  | H | 8.00 | 7.95 |
|  |  |  |  | N | 3.96 | 3.95 |
|  |  |  |  | P | 8.76 | 8.68 |
| 55 | 77 | 83.1 | $n_D^{20.0}$ 1.5261 | C | 49.01 | 48.79 |
|  |  |  |  | H | 8.24 | 8.26 |
|  |  |  |  | N | 3.81 | 3.76 |
|  |  |  |  | P | 8.43 | 8.31 |
| 56 | 78 | 82.6 | $n_D^{20.0}$ 1.5240 | C | 50.36 | 50.39 |
|  |  |  |  | H | 8.47 | 8.38 |
|  |  |  |  | N | 3.67 | 3.67 |
|  |  |  |  | P | 8.12 | 7.87 |
| 57 | 79 | 80.9 | $n_D^{22.5}$ 1.5281 | C | 50.36 | 50.07 |
|  |  |  |  | H | 8.47 | 8.37 |
|  |  |  |  | N | 3.67 | 3.74 |
|  |  |  |  | P | 8.12 | 8.16 |
| 58 | 80 | 80.5 | $n_D^{18.0}$ 1.5235 | C | 51.61 | 51.40 |
|  |  |  |  | H | 8.68 | 8.45 |
|  |  |  |  | N | 3.54 | 3.60 |
|  |  |  |  | P | 7.83 | 7.67 |
| 59 | 81 | 85.1 | $n_D^{22.0}$ 1.5390 | C | 49.28 | 49.24 |
|  |  |  |  | H | 7.74 | 7.76 |
|  |  |  |  | N | 3.83 | 3.84 |
|  |  |  |  | P | 8.47 | 8.28 |
| 60 | 82 | 81.1 | $n_D^{22.0}$ 1.5393 | C | 43.57 | 43.43 |
|  |  |  |  | H | 6.54 | 6.88 |
|  |  |  |  | N | 3.63 | 3.91 |
|  |  |  |  | P | 8.02 | 8.22 |
| 61 | 83 | 80.8 | $n_D^{21.0}$ 1.5329 | C | 45.99 | 46.04 |
|  |  |  |  | H | 7.74 | 7.72 |
|  |  |  |  | N | 4.13 | 4.11 |
|  |  |  |  | P | 9.12 | 9.01 |
| 62 | 84 | 81.9 | $n_D^{22.5}$ 1.5272 | C | 47.56 | 47.48 |
|  |  |  |  | H | 8.00 | 7.98 |
|  |  |  |  | N | 3.96 | 3.98 |
|  |  |  |  | P | 8.76 | 8.57 |
| 63 | 85 | 81.5 | $n_D^{22.0}$ 1.5230 | C | 49.02 | 49.24 |
|  |  |  |  | H | 8.23 | 8.39 |
|  |  |  |  | N | 3.81 | 3.81 |
|  |  |  |  | P | 8.43 | 8.51 |
| 64 | 86 | 82.2 | $n_D^{22.0}$ 1.5204 | C | 50.37 | 50.43 |
|  |  |  |  | H | 8.45 | 8.42 |
|  |  |  |  | N | 3.67 | 3.64 |
|  |  |  |  | P | 8.12 | 7.84 |
| 65 | 87 | 82.7 | $n_D^{23.0}$ 1.5245 | C | 50.36 | 50.58 |
|  |  |  |  | H | 8.47 | 8.58 |
|  |  |  |  | N | 3.67 | 3.78 |
|  |  |  |  | P | 8.12 | 8.11 |
| 66 | 88 | 83.1 | $n_D^{22.5}$ 1.5232 | C | 50.36 | 50.37 |
|  |  |  |  | H | 8.47 | 8.49 |
|  |  |  |  | N | 3.67 | 3.68 |
|  |  |  |  | P | 8.12 | 8.06 |
| 67 | 89 | 82.7 | $n_D^{23.0}$ 1.5220 | C | 51.63 | 50.67 |
|  |  |  |  | H | 8.68 | 8.66 |
|  |  |  |  | N | 3.54 | 3.51 |
|  |  |  |  | P | 7.83 | 7.89 |
| 68 | 90 | 85.4 | $n_D^{19.5}$ 1.5212 | C | 51.63 | 51.65 |
|  |  |  |  | H | 8.68 | 8.66 |
|  |  |  |  | N | 3.54 | 3.54 |
|  |  |  |  | P | 7.83 | 7.71 |
| 69 | 91 | 84.6 | $n_D^{22.0}$ 1.5362 | C | 49.28 | 48.89 |
|  |  |  |  | H | 7.74 | 7.57 |
|  |  |  |  | N | 3.83 | 3.84 |
|  |  |  |  | P | 8.47 | 8.04 |
| 70 | 92 | 84.2 | $n_D^{22.5}$ 1.5248 | C | 49.01 | 49.09 |
|  |  |  |  | H | 8.24 | 8.26 |
|  |  |  |  | N | 3.81 | 3.95 |
|  |  |  |  | P | 8.43 | 7.87 |
| 71 | 93 | 83.5 | $n_D^{22.5}$ 1.5241 | C | 50.36 | 50.37 |
|  |  |  |  | H | 8.47 | 8.37 |
|  |  |  |  | N | 3.67 | 3.60 |
|  |  |  |  | P | 8.12 | 8.08 |
| 72 | 94 | 81.6 | $n_D^{22.5}$ 1.5225 | C | 50.36 | 50.46 |
|  |  |  |  | H | 8.47 | 8.49 |
|  |  |  |  | N | 3.67 | 3.63 |
|  |  |  |  | P | 8.12 | 7.97 |
| 73 | 95 | 82.1 | $n_D^{21.5}$ 1.5199 | C | 51.61 | 51.90 |
|  |  |  |  | H | 8.68 | 8.61 |
|  |  |  |  | N | 3.54 | 3.85 |
|  |  |  |  | P | 7.83 | 7.55 |
| 74 | 96 | 80.1 | $n_D^{21.5}$ 1.5220 | C | 51.61 | 61.12 |
|  |  |  |  | H | 8.68 | 9.12 |
|  |  |  |  | N | 3.54 | 3.51 |
|  |  |  |  | P | 7.83 | 7.66 |
| 75 | 97 | 81.8 | $n_D^{21.5}$ 1.5221 | C | 51.61 | 51.46 |
|  |  |  |  | H | 8.68 | 8.67 |
|  |  |  |  | N | 3.54 | 3.91 |
|  |  |  |  | P | 7.83 | 7.57 |
| 76 | 98 | 81.5 | $n_D^{21.0}$ 1.5205 | C | 52.77 | 52.81 |
|  |  |  |  | H | 8.88 | 8.72 |
|  |  |  |  | N | 3.42 | 3.18 |
|  |  |  |  | P | 7.56 | 7.33 |
| 77 | 99 | 82.3 | $n_D^{22.5}$ 1.5171 | C | 52.77 | 52.56 |
|  |  |  |  | H | 8.88 | 8.61 |
|  |  |  |  | N | 3.42 | 3.13 |
|  |  |  |  | P | 7.56 | 7.41 |
| 78 | 100 | 84.1 | $n_D^{25.5}$ 1.5270 | C | 44.29 | 44.12 |
|  |  |  |  | H | 7.43 | 7.46 |
|  |  |  |  | N | 4.30 | 4.29 |
|  |  |  |  | P | 9.52 | 9.58 |

What we claim is:
1. A compound of the formula

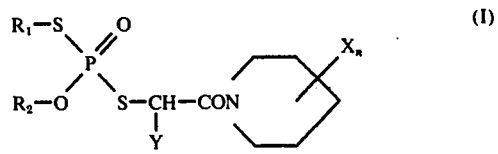

(I)

wherein $R_1$ is lower alkyl, lower alkenyl, lower alkynyl, cycloalkyl having up to 6 carbon atoms, phenyl $C_1$-$C_2$ alkyl, and phenyl $C_1$-$C_2$ alkyl substituted with halogen or lower alkyl or halogen substituted alkenyl having up to 3 carbon atoms; $R_2$ is lower alkyl; Y is hydrogen or methyl, X is lower alkyl and n is an integer of 1 to 5.

2. A compound of the formula,

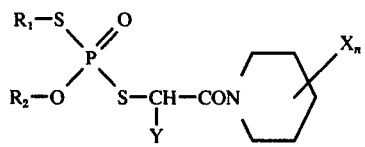

wherein $R_1$ is $C_1$ - $C_8$ straight or branched chain alkyl, allyl, chloroallyl, methallyl, propargyl, cyclohexyl, benzyl, α-methylbenzyl, phenethyl, β-methylphenethyl, chlorobenzyl, dichlorobenzyl, bromobenzyl or $C_1$ - $C_4$ alkyl substituted benzyl; $R_2$ is $C_1$ - $C_4$ alkyl; Y is hydrogen or methyl; X is methyl or ethyl; n is an integer of 1 to 3.

3. A compound of the formula,

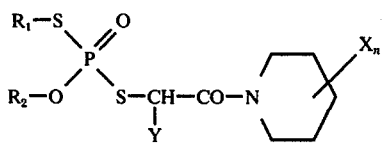

wherein $R_1$ is lower alkyl, cycloalkyl, lower alkenyl, halogen-substituted alkenyl, lower alkynyl or phenyl lower alkyl group; $R_2$ is lower alkyl; Y is hydrogen or methyl; X is lower alkyl; n is an integer of 1 to 3.

4. A compound of the formula,

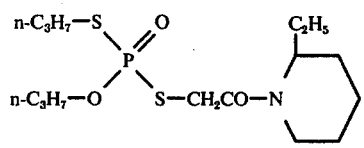

5. A compound of the formula,

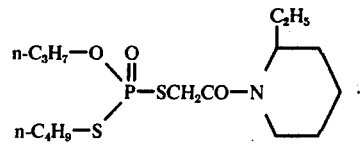

6. A compound of the formula,

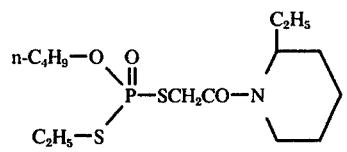

7. A compound of the formula,

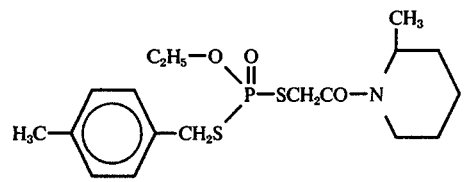

8. A compound of the formula,

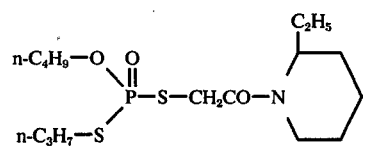

9. A compound of the formula,

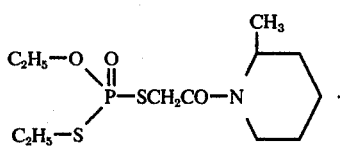

10. A pesticidal composition comprising an inert carrier and a pesticidal amount of at least one phosphorothiolate compound of the formula

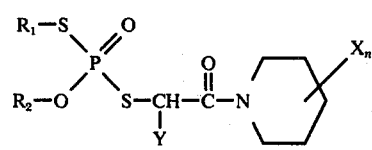

(I)

wherein $R_1$ is lower alkyl, lower alkenyl, lower alkynyl, cycloalkyl having up to 6 carbon atoms, phenyl $C_1$-$C_2$ alkyl, and phenyl $C_1$-$C_2$ alkyl substituted with halogen or lower alkyl or halogen substituted alkenyl having up to 3 carbon atoms; $R_2$ is lower alkyl; Y is hydrogen or methyl, X is lower alkyl and n is an integer of 1 to 5.

11. A pesticidal composition of claim 10, wherein the composition is in the form of granules, dusts, wettable powders, emulsifiable concentrates or fine granules.

12. A pesticidal composition of claim 11, wherein the composition further contains fertilizers, fungicides, insecticides, nematocides or herbicides or a combination thereof.

13. A method for killing bad weeds, injurious insects, nematodes and acarides, which comprises applying an effective amount of a compound embraced by formula (I) in claim 17.

* * * * *